(12) United States Patent
Oliver et al.

(10) Patent No.: US 8,070,765 B2
(45) Date of Patent: Dec. 6, 2011

(54) SYSTEMS AND METHODS FOR SURGICAL REMOVAL OF BRAIN TUMORS

(75) Inventors: Dana A. Oliver, Jacksonville, FL (US); Louis M. Shadeck, Jacksonville, FL (US); Robert F. Spetzler, Paradise Valley, AZ (US)

(73) Assignee: Medtronic Xomed, Inc., Jacksonville, FL (US)

( * ) Notice: Subject to any disclaimer, the term of this patent is extended or adjusted under 35 U.S.C. 154(b) by 383 days.

(21) Appl. No.: 12/361,037

(22) Filed: Jan. 28, 2009

(65) Prior Publication Data

US 2010/0191266 A1 Jul. 29, 2010

(51) Int. Cl.
*A61B 17/32* (2006.01)
*A61B 17/20* (2006.01)

(52) U.S. Cl. .................................... 606/171; 604/22

(58) Field of Classification Search .............. 604/22, 604/164.01, 164.02, 164.06, 164.09, 164.11, 604/264, 272; 606/167, 169–171, 180
See application file for complete search history.

(56) References Cited

U.S. PATENT DOCUMENTS

| | | | | |
|---|---|---|---|---|
| 3,844,272 A * | 10/1974 | Banko | ............ | 600/566 |
| 4,368,734 A * | 1/1983 | Banko | ............ | 606/170 |
| 4,517,977 A | 5/1985 | Frost | | |
| 4,598,710 A * | 7/1986 | Kleinberg et al. | ............ | 606/170 |
| 5,217,478 A | 6/1993 | Rexroth | | |
| 5,712,543 A | 1/1998 | Sjostrom | | |
| 6,001,116 A * | 12/1999 | Heisler et al. | ............ | 606/180 |
| 6,017,354 A | 1/2000 | Culp et al. | | |
| 6,037,724 A | 3/2000 | Buss et al. | | |
| 6,090,123 A | 7/2000 | Culp et al. | | |
| 6,159,175 A * | 12/2000 | Strukel et al. | ............ | 604/22 |
| 6,500,169 B1 | 12/2002 | Deng | | |
| 6,652,488 B1 | 11/2003 | Cover et al. | | |
| 6,979,332 B2 | 12/2005 | Adams | | |
| 2005/0054972 A1 | 3/2005 | Adams et al. | | |

OTHER PUBLICATIONS

Shadeck, U.S. Appl. No. 12/044,644, filed Mar. 7, 2008 and entitled "Systems and Methods for Surgical Removal of Tissue"; 46 pgs.

* cited by examiner

*Primary Examiner* — Nicholas Lucchesi
*Assistant Examiner* — Nathan R Price
(74) *Attorney, Agent, or Firm* — Dicke, Billig & Czaja, PLLC

(57) ABSTRACT

A method for treating a brain tumor includes providing a surgical instrument having an inner member and an outer member. The outer member has a distal region forming a cutting window. The inner member is rotatably received within the outer member, and has a cutting tip that is exposed at the window. The cutting tip and the distal region of the outer member combine to define a cutting implement. An opening is created through the patient's skull to provide access to a brain tumor target site. The cutting implement is delivered through the opening to the target site. The cutting tip is placed into contact with the tumor and operated to cut the tumor. The target site is selectively aspirated to remove cut tumor tissue.

23 Claims, 13 Drawing Sheets

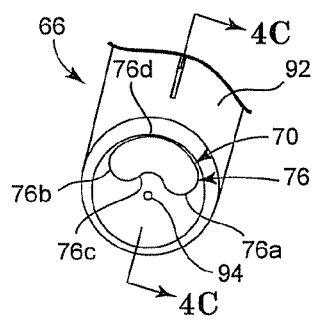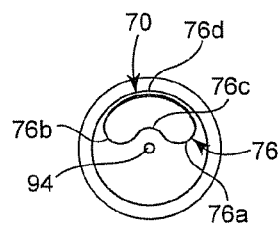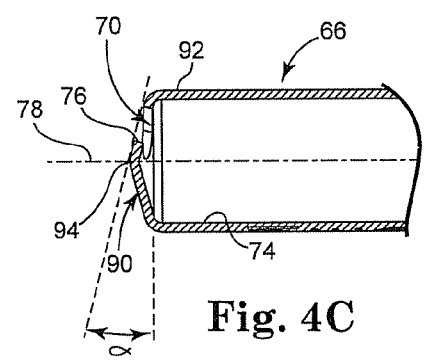
Fig. 4A
Fig. 4B
Fig. 4C

SYSTEMS AND METHODS FOR SURGICAL REMOVAL OF BRAIN TUMORS

BACKGROUND

The present disclosure relates to treatment of brain tumors. More particularly, it relates to surgical systems, instruments, and methods useful in reducing and/or removing brain tumors.

Brain surgery is the treatment of choice for accessible brain tumors. The goal of surgery is to remove as much tumor tissue as possible. The most commonly performed surgery for removal of a brain tumor is a craniotomy. In general, the neurosurgeon makes an incision into the scalp, cranium, dura, meninges, and cortex to expose an area of brain over the tumor. Location and removal of the tumor then takes place. In this regard, a variety of surgical instruments, such as a cavitational ultrasonic surgical aspirator (CUSA) or a surgical laser knife, are commonly used.

The delicate tissues associated with the human brain anatomy give rise to several concerns when using a CUSA, laser knife, or other brain surgery instrument. By way of reference, the brain is covered by three membranes or meninges that in turn are surrounded by the skull. The three layers of meninges are the dura mater (immediately beneath the skull), the arachnoid, and the pia mater. Spinal fluid flows in the space between the arachnoid and the pia mater membranes, known as the subarachnoid space. These meninges are thin and delicate, with the pia mater carrying or maintaining the many blood vessels associated with the brain. Due to the friable nature of especially the pia mater, neurosurgeons must exercise great care when attempting to surgically remove a brain tumor; unintended damage to the pia mater can diminish the primary blood supply to the brain. Unnecessary injury to other healthy structures, such as the arachnoid or brain tissue (e.g., cerebral cortex) can also lead to patient impairment. With this in mind, CUSA instruments deliver ultrasonic action to remove tissue and bone. The surgeon attempts to place the ultrasonic cutting tip against tissue to be destroyed. However, high frequency cutting may also occur and damage tissue surrounding the targeted tumor when touched by the instrument's shaft. Further, due to the relatively large size of the CUSA handpiece, it may be difficult to visually confirm placement of the ultrasonic shaft/tip. Similarly, use of a laser knife may give rise to unintended tissue damage due to local heat in and around the incision line.

In light of the above, a need exists for surgical systems and methods for reducing or removing brain tumors while minimizing likelihood of normal tissue damage.

SUMMARY

Some aspects in accordance with principles of the present disclosure relate to a surgical method for surgically treating a brain tumor of a patient. The method includes providing a surgical system including a surgical instrument having an inner member and an outer member. The inner member includes a distal cutting tip, whereas the outer member has a distal region forming a cutting window. The cutting window is defined by two semicircular end portions connected by two arcuate portions. In this regard, the inner member is rotatably received within the outer member such that the cutting tip is exposed at the cutting window. Further, the cutting tip and the distal region of the outer member combine to define a cutting implement. With this in mind, an opening is created through a skull of the patient to provide external access to a target site at which the brain tumor is located. The cutting implement is delivered through the opening to the target site. The distal cutting tip is positioned so as to remove the tumor and tissue of the target site. The inner member is then moved relative to the outer member, thereby causing the cutting tip to cut tissue of the tumor. Finally, the target site is selectively aspirated to remove the cut or debrided tumor tissue. By using the distal cutting tip through the cutting window to at least partially isolate the tumor and selectively aspirating the target site, the likelihood of damaging normal tissue is minimized. In some alternative aspects, methods of the present disclosure further include varying a level of vacuum (or aspiration rate) at the target site throughout the procedure, with the tumor being drawn into contact with the cutting tip via applied aspiration prior to a cutting operation.

Other aspects in accordance with the present disclosure relate to a surgical system for debriding a brain tumor. The system includes a surgical cutting instrument, a motor, and a source of negative pressure. The cutting instrument includes an inner member, an outer member, a handpiece, and an aspiration control device. The inner member includes a distal cutting tip, whereas the outer member has a distal region forming a cutting window. The cutting window is defined by two semicircular end portions connected by two arcuate portions. The handpiece maintains the inner and outer members such that the inner member is rotatably received within the outer member, with the cutting tip being exposed at the cutting window. Further, the cutting tip and the distal region combine to define a cutting implement. The aspiration control device is maintained by the handpiece. The motor is connected to the inner member for moving the inner member relative to the outer member, for example as part of a cutting operation. Finally, the source of negative pressure is fluidly connected to the cutting implement via a fluid pathway. With this in mind, the aspiration control device is fluidly connected to the fluid pathway for providing user control over a level of vacuum applied at the cutting implement. The above system is highly useful in performing brain tumor surgery, affording the neurosurgeon the ability to more precisely effectuate cutting only of the brain tumor, as well as to control aspiration applied to the target site. With some alternative constructions in accordance with principles of the present disclosure, the surgical instrument further includes a control assembly configured to allow selective rotation of the outer member relative to the inner member.

Yet other aspects in accordance with the present disclosure relate to a surgical system for debriding a brain tumor, including a surgical cutting instrument, a motor, and a source of negative pressure. The cutting instrument includes an inner member, an outer member, a handpiece, and an aspiration control device. The inner member includes a distal cutting tip, whereas the outer member has a distal region forming a cutting window. The distal cutting tip includes a distal surface that is conically shaped and the distal region also includes a distal surface that is conically shaped. The handpiece maintains the inner and outer members such that the inner member is rotatably received within the outer member, the cutting tip being exposed at the cutting window. Further, the cutting tip and the distal region combine to define a cutting implement. The aspiration control device is maintained by the handpiece. The motor is connected to the inner member for moving the inner member relative to the outer member, for example as part of a cutting operation. Finally, the source of negative pressure is fluidly connected to the cutting implement via a fluid pathway. With this in mind, the aspiration control device is fluidly connected to the fluid pathway and forms a user interface opening that is open to ambient. With this construction, the user interface opening is adapted to provide user control over a level of vacuum applied at the cutting implement. For example, by obstructing more or less of the interface opening, the level of vacuum applied at the cutting implement is increased or decreased, respectively. With some alternative constructions in accordance with principles of the present disclosure, the system is configured such that when the source of negative pressure is generating negative pressure and the user interface hole is exteriorly unobstructed, a level of vacuum applied at the cutting implement is substantially zero.

BRIEF DESCRIPTION OF THE DRAWINGS

FIG. 4A is an enlarged, perspective view of a distal region of an outer tubular member of the assembly of FIG. 3;

FIG. 4B is a front view of the distal region of FIG. 4A;

FIG. 4C is a cross-sectional view of the distal region of FIG. 4B along the line 4C-4C;

DETAILED DESCRIPTION

Figure 1:
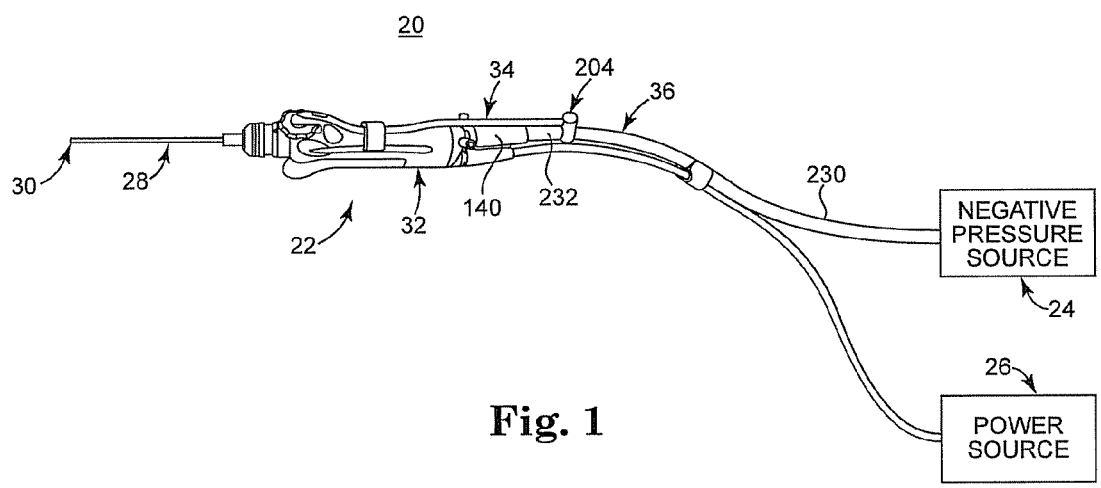
FIG. 1 is a schematic illustration of a system for surgically reducing or removing a brain tumor in accordance with principles of the present disclosure.

A surgical system 20 in accordance with aspects of the present disclosure for use in debriding a brain tumor as part of brain surgery is shown in FIG. 1. The system 20 includes a surgical cutting instrument 22, a source of negative pressure 24, and a power source 26. Details on the various components are provided below. In general terms, however, the surgical instrument 22 includes a blade assembly 28 forming a cutting implement 30 (referenced generally), a handpiece 32, and an aspiration control device 34. The source of negative pressure 24 is fluidly connected to the cutting implement 30 via a fluid pathway 36 extending through the handpiece 32. The aspiration control device 34 is also fluidly connected to the fluid pathway 36. Finally, the power source 26 is electrically connected to a motor (not shown) maintained by the handpiece 32. During use in surgically reducing or removing a brain tumor, the cutting implement 30 is deployed to a target site, with the user manipulating the handpiece 32 to achieve a desired position of the cutting implement 30 relative to the brain tumor. The power source 26 energizes the motor to effectuate a tumor cutting operation at the cutting implement 30. Finally, the aspiration control device 34 is manually operated by the user to selectively effectuate aspiration at the cutting implement 30 via a vacuum generated by the source of negative pressure 24. In some configurations, the aspiration control device 34 affords the user the ability to vary the rate or level of aspiration, as well as an aggressiveness of cutting at the cutting implement 30.

Figure 2:
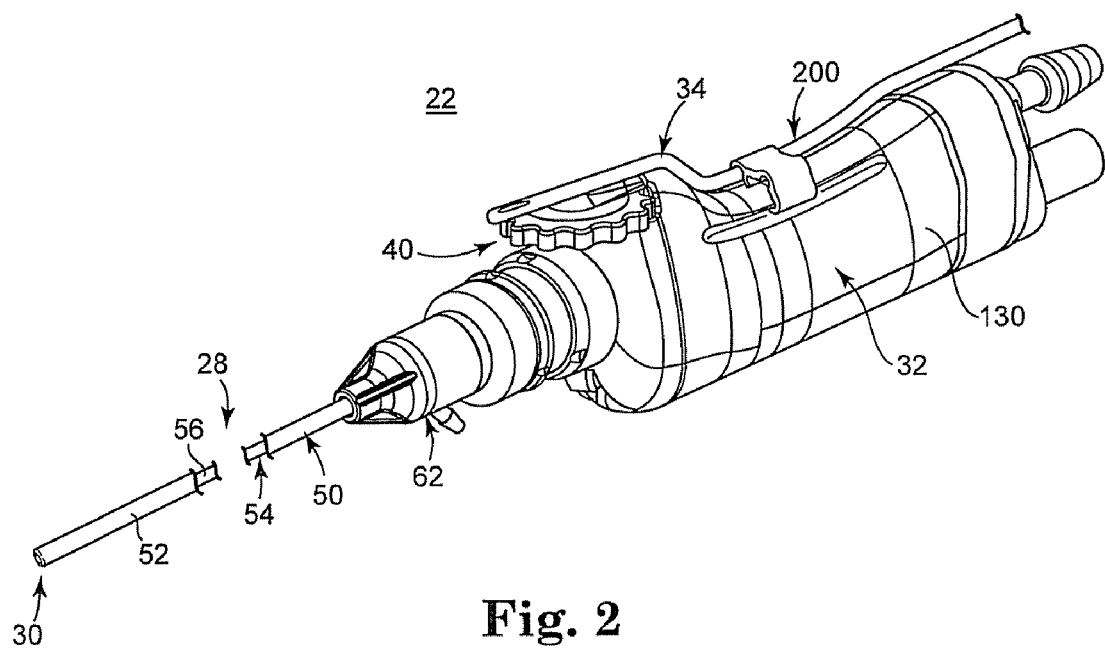
FIG. 2 is a perspective view of a surgical instrument useful with the system of FIG. 1.

With the above general construction of the system 20 in mind, features associated with the surgical instrument 22 in accordance with aspects of the present disclosure are shown in greater detail in FIG. 2. The surgical instrument 22 includes the blade assembly 28, the handpiece 32, and the aspiration control device 34 as mentioned above. In addition, in some embodiments, the surgical instrument 22 includes an optional control assembly 40 (referenced generally) configured to provide user control over a rotational position of a component of the blade assembly 28 as described below.

The blade assembly 28 can assume a variety of forms, and in some configurations includes an outer member assembly 50 having an outer member 52, and an inner member assembly 54 having an inner member 56. In general terms, the inner member 56 is rotatably disposed within the outer member 52, with other components of the assemblies 50, 54 effectuating connection to the handpiece 32. Regardless, the outer and inner members 52, 56 extend distally from the handpiece 32, and combine to form the cutting implement 30 as described below. As a point of reference, while the blade assembly 28 is shown as including two of the members 52, 56, in other configurations, three or more co-axially assembled members can be provided. Further, the blade assembly 28, and in particular the members 52, 56, can have a linear or straight configuration as shown, or can alternately have a curved construction (such as by the inclusion of a curved member encompassing at least a portion of the outer member 52).

Figure 3:
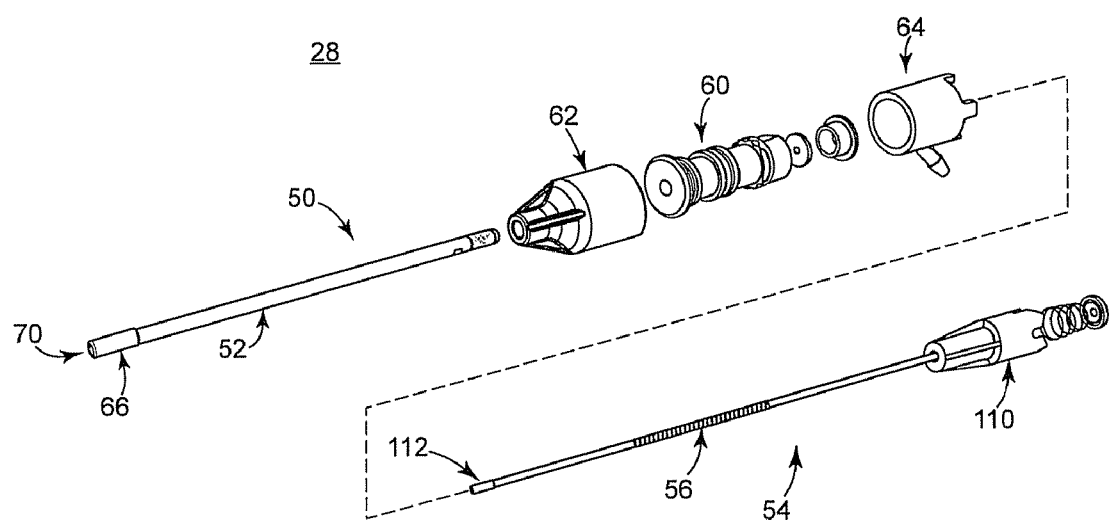
FIG. 3 is an exploded view of a blade assembly portion of the instrument of FIG. 2.

With further reference to FIG. 3, with some configurations, in addition to the outer member 52, the outer member assembly 50 includes an outer member hub 60, a collet 62, and an optional irrigation hub 64. The outer member 52 is secured to the outer member hub 60, with the collet 62 facilitating attachment to the handpiece 32. Further, where provided, the irrigation hub 64 facilitates delivery of an irrigation fluid to the outer member 52. Other constructions appropriate for assembling the outer member 52 to the handpiece 32 are also acceptable. Regardless, the outer member 52 is tubular in some embodiments, and forms a distal region 66. The distal region 66, in turn, forms in some configurations a cutting window 70.

The distal region 66 can be an integrally formed component of the outer member 52, or can be separately formed and assembled to other components (e.g., the distal region 66 can be formed and then attached to an appropriately sized, rigid metal tube in completing the outer member 52). Regardless, one construction of the distal region 66 in accordance with principles of the present disclosure is shown in greater detail in FIGS. 4A-4C. As best shown in FIG. 4C, the distal region 66 forms a lumen 74 that is otherwise open at the cutting window 70. The cutting window 70 is positioned at the distal-most portion of the distal region 66. With this mind, the cutting window 70 is defined by a cutting window wall 76. As best shown in FIGS. 4A and 4B, the cutting window 70 can have a kidney-like shape. In particular, the cutting window wall is defined by two semicircular end portions 76a, 76b connected by two arcuate wall portions 76c, 76d. In the embodiment illustrated, the two arcuate wall portions 76c, 76d are defined about a central axis 78 of the distal region 66. The cutting window 70 can take other forms, as desired. For example, the ends of the window can form other shapes, such as squares, triangles, rectangles, polygons, etc. Additionally, the arcuate portions can be linear or include linear components, in other embodiments.

The cutting window wall 76 is formed from a distal surface 90 that is generally conical in shape. In particular, the distal surface 90 extends from a tubular surface 92 of distal region 66 to a tip end 94. Distal surface 90 extends from tubular surface 92 at an angle α from a distal axis 96 perpendicular to axis 78 and positioned at a distal-most end of tubular surface 92, which, in the embodiment illustrated, is approximately 15°. Additionally, cutting window wall 76 forms the cutting window 70 at the same angle. Distal surface 90 can be adjusted to various other configurations. For example, distal surface 90, in other embodiments, can be perpendicular to tubular surface 92 (i.e., parallel with respect to axis 96), substantially perpendicular to tubular surface 92 and/or at various angles. The angle of distal surface 90 with respect to axis 96 can be in a range of 0° to 45°, 5° to 25° or 10° to 20° in other examples. As a result, the cutting window 70 can extend at the same or similar angles.

Figure 5:
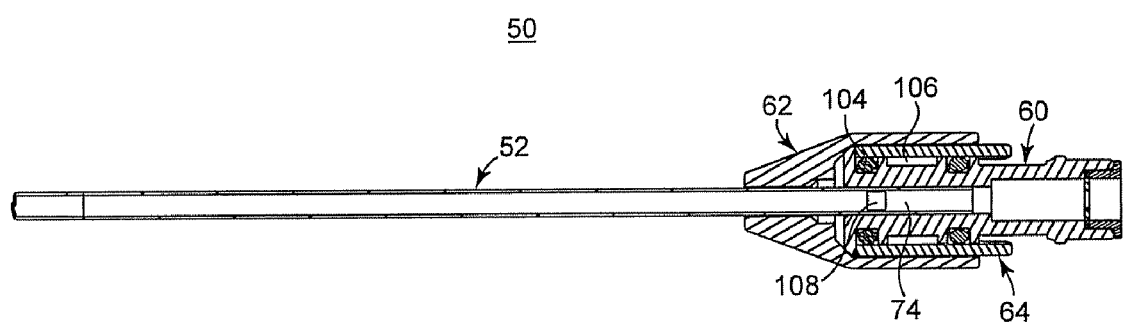
FIG. 5 is a cross-sectional view of the outer member assembly of FIG. 3 upon final construction.

Final construction of the outer member assembly 50 is shown in FIG. 5. The outer member 52 is assembled to the outer member hub 60 that in turn is received within the irrigation hub 64. In this regard, seals 104 (e.g., O-rings) can be provided to effectuate a fluid-tight seal between the irrigation hub 64 and the outer member hub 60. With this construction, then, an irrigation liquid (not shown) can be delivered to the lumen 74 of the outer member 52 via a sealed gap 106 between the hubs 60, 64 and a bore 108 formed in the outer member 52. The assembled hubs 60, 64 are coaxially received with the collet 62, with the outer member 52 extending distal the collet 62 as shown. Other constructions capable of effectuating flow of irrigation liquid to the outer member 52 are also envisioned; in yet other configurations, the irrigation hub 64 (as well as any other irrigation component) can be eliminated.

Figure 6A:
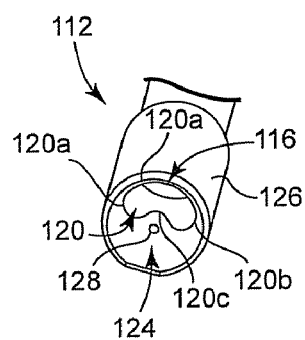
FIG. 6 is an enlarged, cross-sectional view of a portion of an inner member portion of the blade assembly of FIG. 3.
Figure 6B:
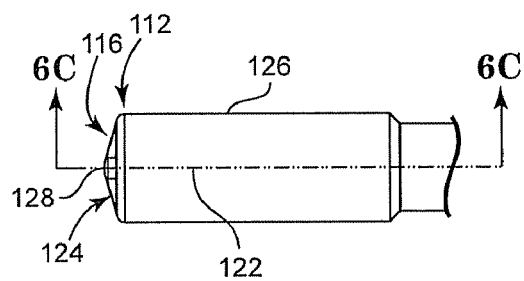
Figure 6C:
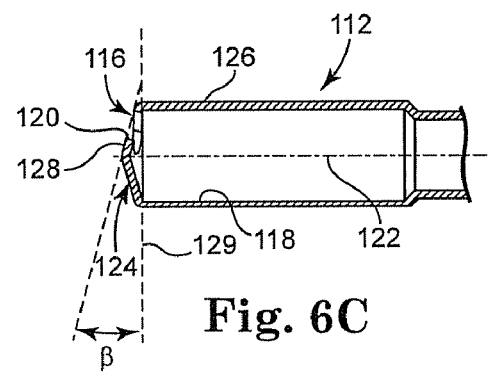

Returning to FIG. 3, the inner member assembly 54 includes the inner member 56, as well as an inner member hub 110. As described below, the inner member hub 110 maintains the inner member 56, and facilitates connection of the inner member assembly 54 to a motor (not shown). Thus, the inner member hub 110 can assume a variety of forms. Regardless, with some constructions, the inner member 56 is tubular, forming a distal cutting tip 112. As shown in FIGS. 6A-C, the cutting tip 112 includes an aperture 116 that is otherwise open to a lumen 118 defined by the inner member 56. As described below, the aperture 116 and the lumen 118 serve as an aspiration outlet of the aspiration fluid pathway 36 (FIG. 1) otherwise employed for aspirating a target site. Alternatively, the cutting tip 112 can assume other forms that may or may not include an aperture fluidly connected to a lumen. For example, the cutting tip 112 can be a closed burr.

In the embodiment illustrated in FIGS. 6A-C, however, the aperture 116 includes a window wall 120 that is substantially similar in shape to cutting window wall 76, including two semicircular portions 120a, 120b connected by two arcuate wall portions 120c, 120d. As illustrated, the two arcuate wall portions 120c, 120d are defined by a central axis 122 of cutting tip 112. Additionally, cutting tip 112 includes a distal surface 124 similar in shape to distal surface 90 of distal region 66. In particular, distal surface 124 is generally conical in shape, extending from a tubular surface 126 to a tip end 128. Distal surface 124 extends at an angle β with respect to a distal axis 129 that is perpendicular to central axis 122 and positioned at a distal-most position of tubular surface 126. Angle β can be adapted to conform to distal surface 90. In the embodiment illustrated, the angle β is 16°. In other embodiments, the distal surface 94 can be perpendicular to tubular surface 126, substantially perpendicular to surface 126 or positioned at other angles. For example, the angle β can be in a range of 0° to 45°, 5° to 25° or 10° to 20°.

Figure 7:
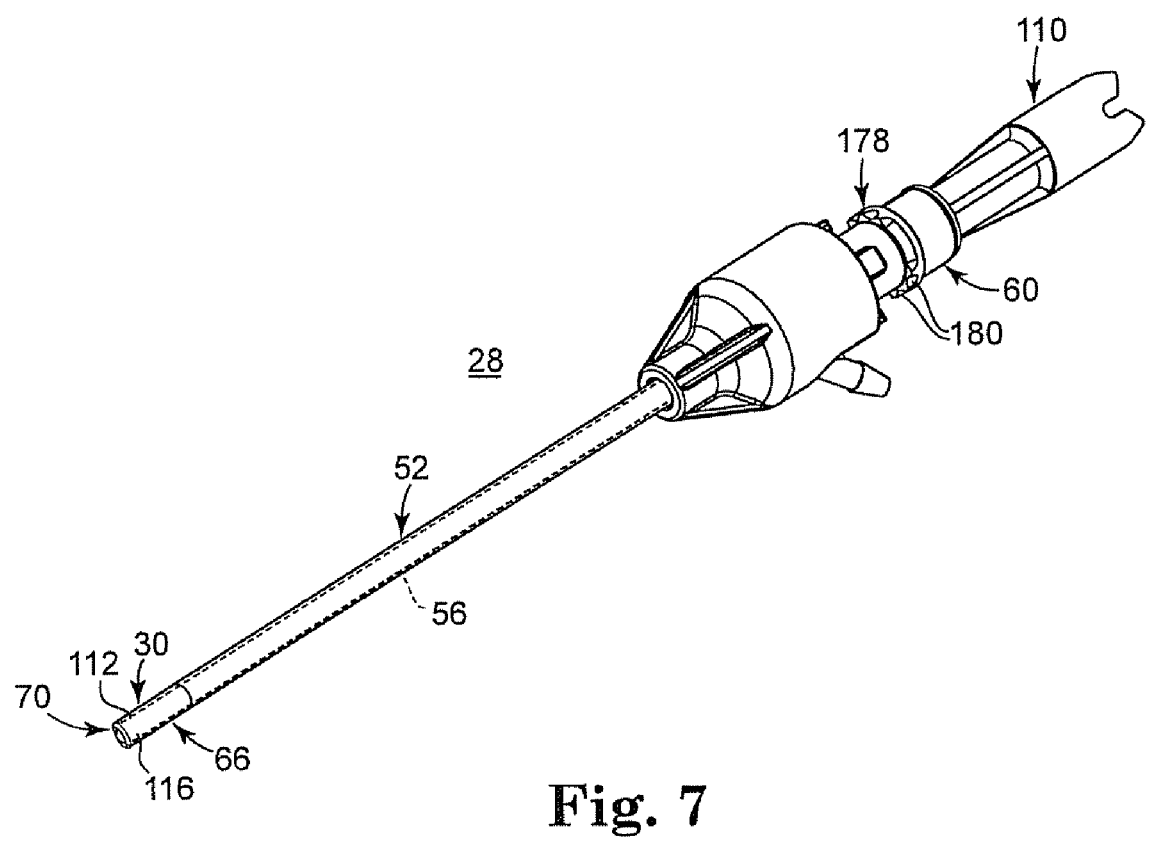
FIG. 7 is a perspective view of the blade assembly of FIG. 3 upon final assembly.

Final construction of the blade assembly 28 is shown in FIG. 7. As a point of reference, while the outer and inner members 52, 56 have been shown in as being linear, in other configurations, one or more bends or curves can be formed and/or additional tubular member(s) provided. The inner member 56 is received within the lumen 74 (FIG. 4C) of the outer member 52, and is attached to the inner member hub 110. The inner member hub 110, in turn, is positioned proximal the outer member hub 60 and is rotatable relative thereto, such that rotation of the inner member hub 110 effectuates rotation of the inner member 56 relative to the outer member 52. Further, the cutting tip 112 of the inner member 56 is positioned at the cutting window 70 of the outer member 52. Thus, the cutting tip 112 is exposed via the cutting window 70 for performing a cutting or debriding procedure. Finally, the distal region 66 of the outer member 52 (e.g., the cutting window 70) combine with the cutting tip 112 to form the cutting implement 30. Aspiration is effectuated at the cutting implement 30 via the aperture 116 provided with the inner member 56 (with the aperture 116 being exteriorly open through the cutting window 70). Alternatively, aspiration or suctioning at the cutting implement 30 can be provided by the outer member 52, a separate tubing carried by the cutting implement 30, etc. Similarly, irrigation is provided at the cutting implement via the outer member 52/cutting window 70, although in other embodiments, an additional irrigation supply tube (carried with or separate from the cutting implement 30) can be provided.

Figure 8:
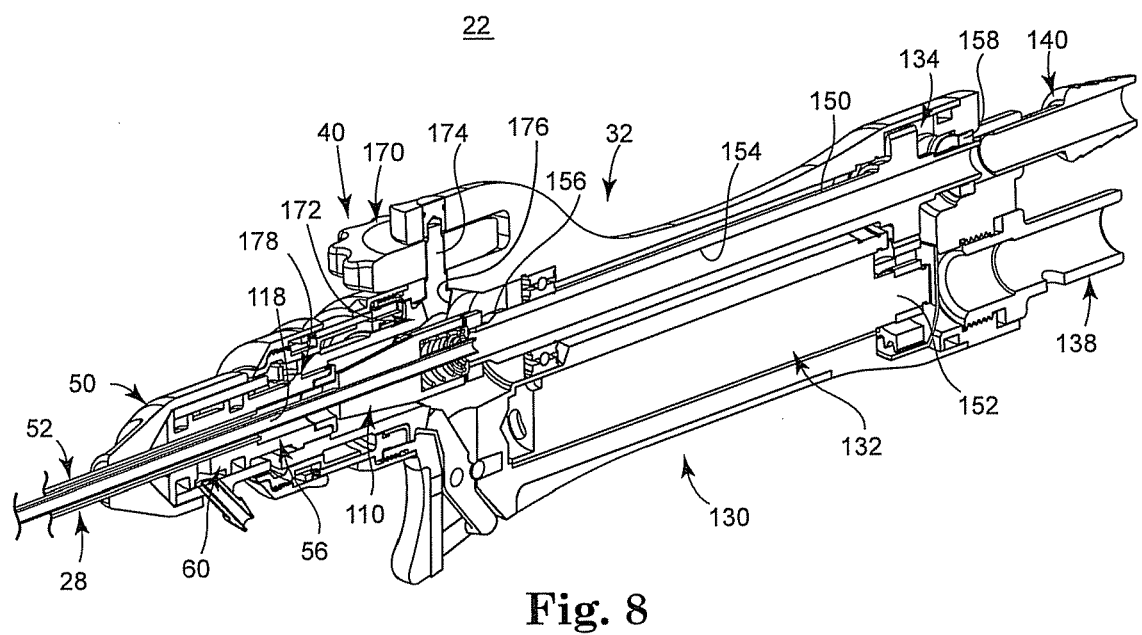
FIG. 8 is a cross-sectional view of a portion of the instrument of FIG. 2.

Returning to FIG. 2, the handpiece 32 can assume a variety of forms that promote manipulation of the blade assembly 28/cutting implement 30 by a user, as well as powered movement of the inner member 56 relative to the outer member 52. For example, FIG. 8 illustrates one construction of the handpiece 32 in accordance with the principles of the present disclosure. As a point of reference, for ease of illustration, the aspiration control device 34 (FIG. 2) is omitted from the view of FIG. 8. Further, the handpiece 32 is shown in FIG. 8 as being assembled to a portion of the blade assembly 28. With this in mind, the handpiece 32 includes a housing 130, the control assembly 40, a motor 132 (shown schematically in FIG. 8), and a drive coupling 134. The motor 132 is secured within the housing 130, with the housing 130 forming a conduit 138 through which wiring (not shown) otherwise providing power to the motor 132 can extend. Further, the housing 130 preferably forms or includes an aspiration port 140 for fluidly connecting the blade assembly 28 to the source of negative pressure 24 (FIG. 1) as described below. The drive coupling 134 mechanically connects the motor 132 to the inner member hub 110, and thus the inner member 56. To this end, a wide variety of constructions can be employed. With some configurations, however, the drive coupling 134 includes an output shaft 150 rotatably linked (e.g., geared) to a drive shaft 152 of the motor 132. The output shaft 150 can assume various forms, and with some constructions forms a passage 154 that, upon final assembly, fluidly connects the aspiration port 140 with a passageway 156 formed by the inner member hub 110 (and thus with the lumen 118 of the inner member 56 otherwise assembled within the passageway 156). Optional dynamic seals 158 can be included to better ensure a fluid-tight seal between the passage 154 and the aspiration port 140.

The optional control assembly 40 facilitates rotation of the outer member 52 relative to the handpiece 32 as described below, and can assume a variety of forms. In some constructions, the control assembly 40 includes an actuator 170 and a translation mechanism 172. The actuator 170 can be akin to a wheel, and is rotatably assembled to the housing 130. The translation mechanism 172 is configured to translate rotation of the actuator 170 to the outer member hub 60, and thus the outer member 52. In some embodiments, the translation mechanism 172 includes a post 174 connected to and extending from the actuator 170. In this regard, an end 176 of the post 174 opposite the actuator 170 (or other intermediate body or bodies interconnecting the post end 176 and the outer member hub 60) is adapted to interface with an engagement feature 178 of the outer member hub 60. More particularly, and as best shown in FIG. 7, in some constructions, the engagement feature 178 of the outer member hub 60 is a series of circumferentially disposed indentations 180. Returning to FIG. 8, the post end 176 is configured to interface with the indentations 180, akin to a ball and detent relationship. With this configuration, then, rotation of the actuator 70 is translated by the post 174 to the outer member hub 60. Rotation of the outer member hub 60, in turn, rotates the outer member 52. Because the outer member hub 60 is not otherwise affixed to other components of the handpiece 32, rotation of the outer member hub 60 results in rotation of the outer member 52 relative to the handpiece 32. Importantly, rotation of the outer member 52 can be achieved by a user without overt movement of the housing 130. The user, while grasping the housing 130 in his or her hand, the surgeon simply rotates the actuator 170 with a finger (or thumb) of the same hand that is otherwise holding the housing 130.

Figure 9A:
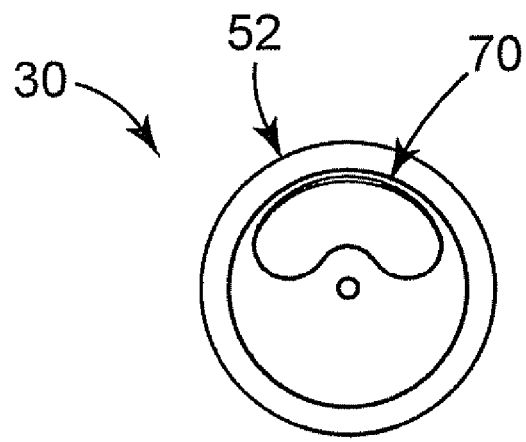
FIGS. 9A and 9B illustrate operation of a cutting implement portion of the instrument of FIG. 8.
Figure 9B:
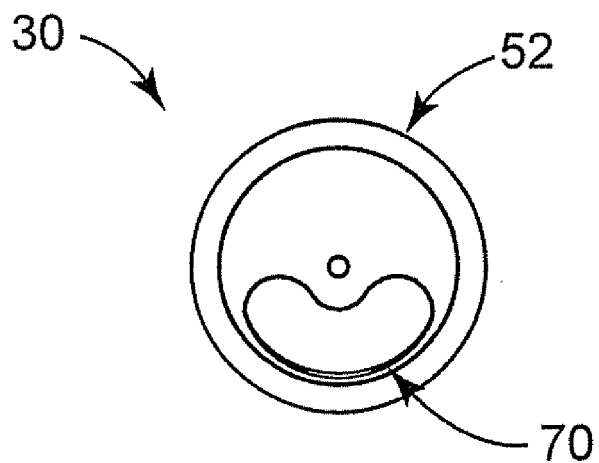

The control assembly 40 can assume a variety of other forms apart from the description provided above, for example as described in U.S. patent application Ser. No. 10/854,020 filed Sep. 22, 2004 and entitled "Surgical Cutting Instrument," the teachings of which are incorporated herein by reference. Conversely, with other constructions of the surgical instrument 22, the control assembly 40 is omitted (i.e., the outer member 52 cannot be independently rotated relative to the handpiece 32). Where provided, however, rotation of the outer member 52 relative to the handpiece 32 allows the user to selectively adjust the position of cutting window 70 so as to provide a desired position for cutting during a brain tumor debridement procedure. For example, as shown in FIG. 9A (in which only a portion of the outer member 52 is illustrated for purposes of clarity), a first rotational position of the outer member 52 relative to the handpiece 32 is shown. The outer member 52 can be rotated relative to the handpiece 32 to a second rotational position, as shown in FIG. 9B. Thus, the outer member 52 can be rotated to position or "face" the cutting window 70 at a desired location (e.g., a brain tumor) without movement of the handpiece 32 (FIG. 8). That is to say, once the cutting implement 30 is delivered to a target site, the precise location at which cutting will occur (i.e., the cutting window 70) can be controlled by movement of the actuator 170 (FIG. 8); the surgeon is not required to contort his or her hand(s) to achieve a desired point of cutting/position of the cutting window 70.

Figure 10:
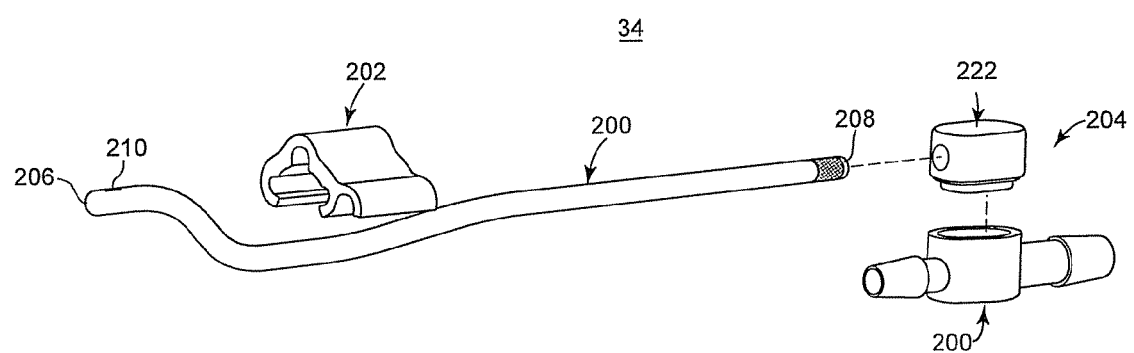
FIG. 10 is an exploded view of an aspiration control device useful with the system of FIG. 1.

Returning to FIG. 2, the aspiration control device 34 can assume a variety of forms, and in some embodiments includes a tube 200 assembled to the housing 130 of the handpiece 32. The tube 200 along with other components of the aspiration control device 34 in accordance with some aspects of the present disclosure is shown in FIG. 10. In addition to the tube 200, the aspiration control device 34 can include a clip 202 and a connector assembly 204. In general terms, the clip 202 connects the tube 200 to the handpiece 32 (FIG. 2). The connector assembly 204 fluidly connects the tube 200 to the fluid pathway 36 (FIG. 1) established with the source of negative pressure 24 (FIG. 1). In still a further embodiment, the aspiration control device 34 can be directly integrated into the handpiece 32. One exemplary configuration of an integrated aspiration control device 34 is described in U.S. patent application Ser. No. 12/044,644, filed on Mar. 7, 2008 and entitled "Systems and Methods for Surgical Removal of Tissue," the teachings of which are incorporated herein by reference.

Figure 11:
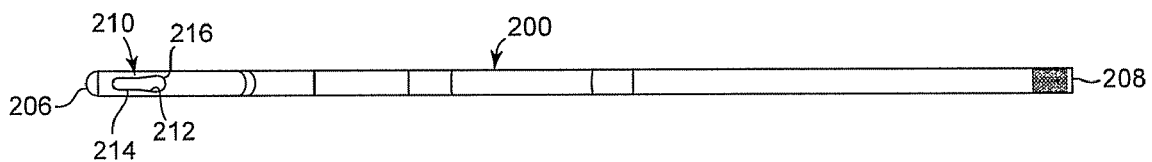
FIG. 11 is a top view of a tube component of the aspiration control device of FIG. 10.

The tube 200 has a shape commensurate with a contour of a surface of the housing 130 (FIG. 2) to which the tube 200 is assembled, and thus may form one or more bends. Regardless, the tube 200 forms a lumen (not shown) extending from a closed, first end 206 to an open, second end 208. Further, the tube 200 forms a user interface hole 210 adjacent the first end 206 that is otherwise fluidly open to the lumen. One construction of the user interface hole 210 is shown in FIG. 11, and is generally sized and shaped to interface with (i.e., be selectively covered by), a user's finger. For example, with some constructions, a perimeter 212 of the user interface hole 210 has a tear drop-like shape, having a relatively linear first segment 214 and an enlarged, rounded second segment 216. This shape generally coincides with a natural shape of an adult's fingertip, although other shapes are also acceptable. As described below, control over the aspiration delivered at the cutting implement 30 (FIG. 1) is selectively effectuated by covering or uncovering the user interface hole 210.

Returning to FIG. 10, the clip 202 can assume a variety of forms adapted to connect the tube 200 to the housing 130 (FIG. 2). In other embodiments, the tube 200 can be permanently affixed to, or formed by (e.g., as an internal bore), the handpiece 32 (FIG. 2), such that the clip 202 can be eliminated.

The connector assembly 204 can also assume a variety of forms, and with some constructions includes a tee connector 220 and a connection block 222. The tee connector 220 is configured for establishing fluid connection with tubing (not shown) between the handpiece 32 (FIG. 1) and the source of negative pressure 24 (FIG. 1). The connection block 222, in turn, is configured for attachment to the second end 208 of the tube 200, as well as to the tee connector 220. Upon final construction, the connector assembly 204 fluidly connects the lumen (not shown) of the tube 200 with the fluid pathway 36 (FIG. 1). A wide variety of other constructions for the connector assembly 204 are equally acceptable.

Returning to FIG. 1, final assembly of the system 20 includes a first tubing 230 extending between, and fluidly connecting, the source of negative pressure 24 and the connector assembly 204. A second tubing 232 fluidly connects the connector assembly 204 with the aspiration port 140 of the handpiece 32. As a result, the fluid pathway 36 is established from the source of negative pressure 24 to the cutting implement 30. More particularly, the source of negative pressure 24 is fluidly connected to the aspiration port 140 via the first tubing 230, the connector assembly 204, and the second tubing 232. The aspiration port 140, in turn, is fluidly connected to the blade assembly 28 via the passage 154 (FIG. 8) of the output shaft 150 (FIG. 8). With some embodiments, the fluid pathway 36 further extends through the lumen 118 (FIG. 6) of the inner member 56 (FIG. 6), and is open at the aperture 116 (FIG. 6). With alternative configurations, the aspiration outlet at the cutting implement 30 can be provided in other forms that may or may not include the aperture 116 of the inner member 56 (e.g., aspiration can be provided via the outer member 52, via a separate tube provided with the blade assembly 28, etc.). Regardless, the tube 200 of the aspiration control device 34 is also in fluid communication with the fluid pathway 36 via the connector assembly 204 with the user interface hole 210 being open to ambient. Thus, the aspiration control device 34 affords the user the ability to control a level of vacuum applied at the cutting implement 30, for example by selectively covering or uncovering the user interface hole 210 (FIG. 11).

A level or rate or vacuum delivered to or experienced at the aperture 116 (FIG. 6A-C), or other aspiration outlet format, will increase as the user interface hole 210 (FIG. 11) is increasingly covered, and vice-versa. With this in mind, the user interface hole 210 has, in some configurations, a larger surface area as compared to the aspiration outlet provided at the cutting implement 30 through which suctioning is otherwise applied. For example, with some constructions, the aspiration outlet provided with the cutting implement 30 is the aperture 116 formed by the inner member 56 (FIG. 3). Commensurate with this description, then, a size of the user interface hole 210 can be selected to be greater than a size of the aperture 116. As a result, when the user interface hole 210 is entirely unobstructed, a vacuum level at the cutting implement 30 (i.e., at the aperture 116) is substantially zero in that the user interface hole 210 provides a path of least resistance for negative pressure within the fluid pathway 36. Further, a user will readily "sense" vacuum or suction at the user interface hole 210, and is thus provided with direct, tactile feedback as to a level of vacuum being applied at the cutting implement 30. Also the user interface hole 210 affords essentially infinite control over the applied vacuum (between zero and maximum generated at the source of negative pressure 24) due to the absence of pre-established indexes or other stop mechanism along the aspiration control device 34.

Figure 12A:
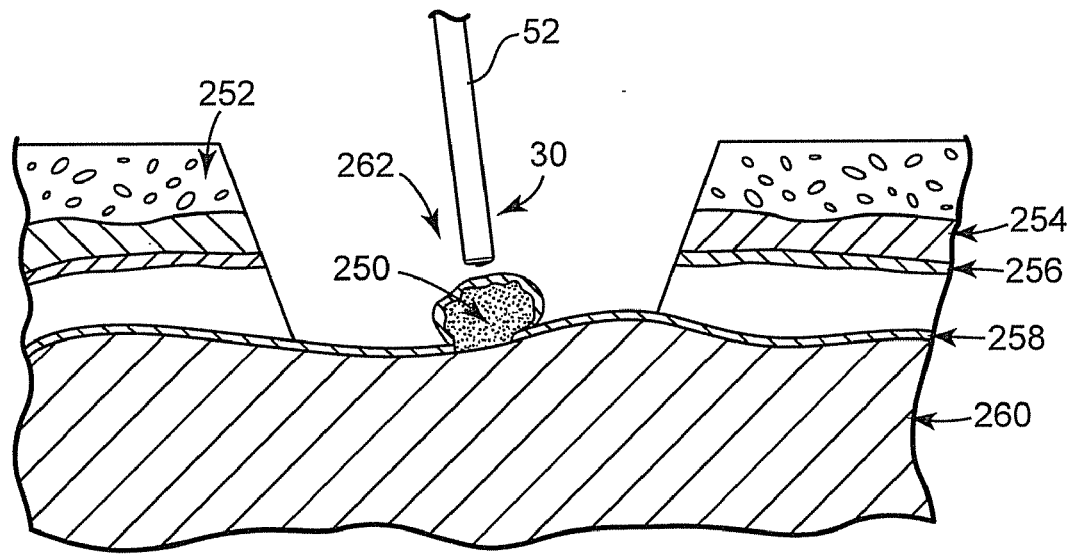
FIGS. 12A and 12B illustrate use of the system of FIG. 1 in surgically removing a brain tumor.

The system 20 is highly useful in the surgical treatment (e.g., removal) of brain tumors (as well as possibly other surgical procedures). In this regard, and with additional reference to FIG. 12A, treatment of a brain tumor 250 in accordance with aspects of the present disclosure includes forming an access opening in the patient's skull 252 (e.g., a conventional craniotomy). As a point of reference, FIG. 12A schematically illustrates other anatomy, including the dura 254, the arachnoid 256, the pia 258, and the cortex 260. The brain tumor 250 is shown as projecting from a natural anatomy of the cortex 260, exteriorly "covered" by the pia 258. With other procedures, the brain tumor 250 may be internal or embedded within the cortex (or other brain tissue) 260. Regardless, once a target site 262 at which the brain tumor 250 is located has been exposed, the system 20 is operated to remove at least some, preferably all, of the brain tumor 250.

The cutting implement 30 is deployed to the target site 262. During delivery of the cutting implement 30, the power supply 26 is inactive, such that the inner member 56 (FIG. 3) does not move relative to the outer member 52. Further, the source of negative pressure 24 may or may not be activated during initial placement of the cutting implement 30. That is to say, a negative pressure condition may or may not be established along the fluid pathway 36. Where the source of negative pressure 24 is activated, however, the user manually effectuates control over delivery of negative pressure to the cutting implement 30, such as by leaving the user interface hole 210 (FIG. 11) associated with the aspiration control device 34 uncovered. As described above, this arrangement causes virtually all of the negative pressure generated by the source of negative pressure 24 to be delivered to the user interface hole 210, and thus not the aspiration outlet/aperture 116 of the cutting implement in a manner that might otherwise negatively impact surrounding tissue of the target site 262.

Once the cutting implement 30 is positioned adjacent the brain tumor 250, the surgeon manipulates the handpiece 32 so as to position the cutting window 70 over the brain tumor 250 and plunge the cutting implement 30 into the brain tumor 250. Where provided, the control assembly 40 can be operated by the surgeon to rotate the cutting window to a desired spatial orientation relative to the target site 262 without overt twisting/contortion of the surgeon's hand(s). Depending upon the particular location of the brain tumor 250, other non-tumor tissue of the brain anatomy may also or alternatively be implicated (e.g., the dura 254, arachnoid 256, cerebral cortex 260, etc.), with the cutting window 70 isolating the brain tumor 250 from this tissue. Further, by controlling (minimizing) aspiration at the cutting implement, unnecessary damage to the pia 258 (and other tissue) is avoided.

Figure 12B:
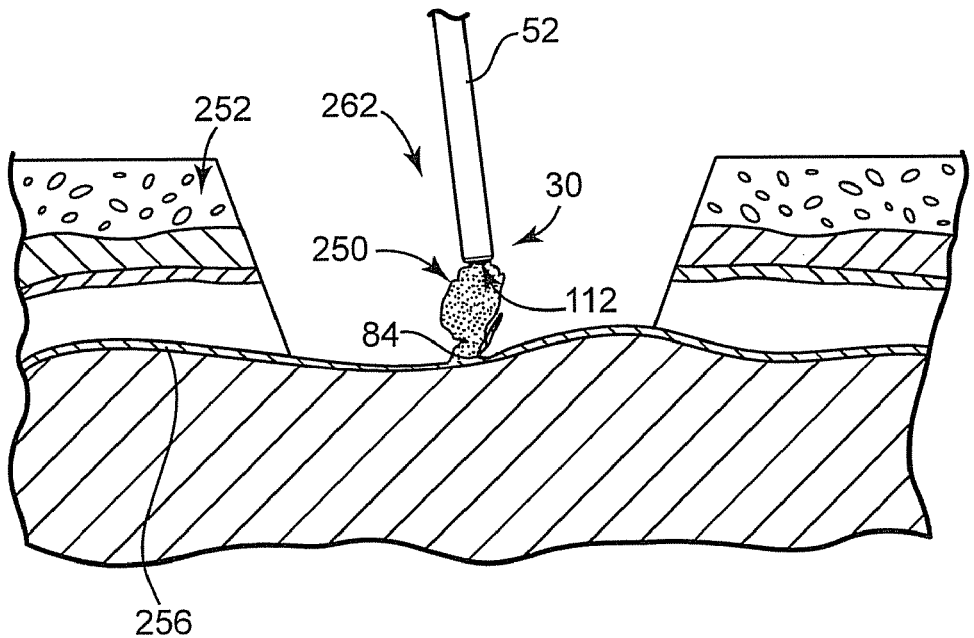

Once the cutting window 70 is desirably positioned, the cutting tip 112 (referenced generally in FIG. 12B) is placed into contact with the brain tumor 250. Further, with some techniques, the aspiration control device 34 is manually operated to effectuate delivery of negative pressure to the cutting implement 30, thus drawing or suctioning the brain tumor 250 into contact with the cutting tip 112. For example, the surgeon can at least partially obstruct the user interface hole 210 (FIG. 11), effectuating a more complete fluid connection between the source of negative pressure 24 and the aspiration aperture 116.

Due to the relatively compact and streamlined size and shape of the handpiece 32, the surgeon can readily, visually confirm desired placement and orientation of the cutting implement 30, and in particular the cutting window 70/cutting tip 112, relative to the brain tumor 250 and the surrounding tissue. Once the surgeon is satisfied with placement of the cutting implement 30, the power supply 26 is activated, thus causing the inner member 56 (FIG. 3) to move relative to the outer member 52. This action, in turn, causes the cutting tip 112 to move within the cutting window 70, cutting or debriding the contacted brain tumor 250. With some constructions, the motor 132 (FIG. 8) operates to rotationally oscillate the cutting tip 112 relative to the cutting window 70. As part of this debriding procedure, the aspiration control device 34 can be manually operated (e.g., movement of the surgeon's finger relative to the hole 210) to effectuate an increased vacuum level at the cutting implement 30, thus removing debrided brain tumor tissue from the target site 262.

During the debriding procedure, the surgeon can periodically confirm continued desired positioning of the cutting implement 30 relative to the brain tumor 250 and the surrounding tissue 256. Where, for example, it is determined that a differing point of cutting along the brain tumor 250 is desired, the outer member 52 can be rotated relative to the inner member 56 (FIG. 3), thereby altering a spatial position of the cutting window 70, and thus a point of contact of the cutting tip 112 with the brain tumor 250. For example, the actuator 170 (FIG. 8) can be manipulated by the user's finger, causing a rotational position of the outer member 52 relative to the inner member 56 to change. Once again, and throughout the entire procedure, the level of vacuum or rate of aspiration can be manually changed at any time by the surgeon, for example by simply covering more or less of the hole 210 (FIG. 11).

Figure 13:
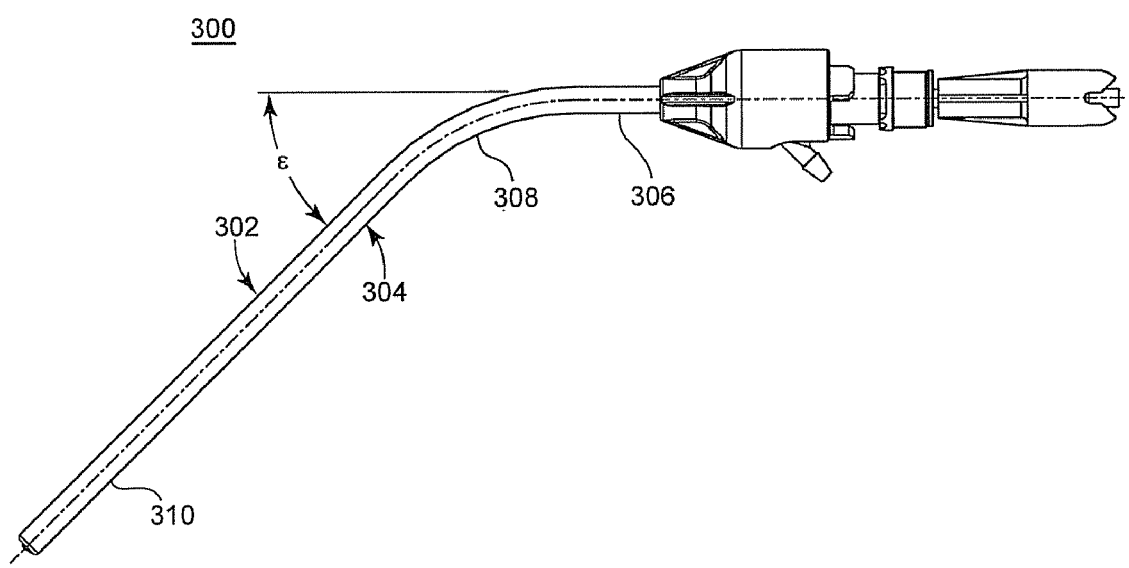
FIG. 13 is a top plan view of a second embodiment of a surgical instrument useful with the system of FIG. 1.

As discussed above, the blade assembly 28, and thus outer member 52 and inner member 56, can include one or more bends as desired. For example, an alternative embodiment of a surgical instrument 300 is illustrated in FIG. 13. As illustrated, the blade assembly 302 of instrument 300 includes an outer tubular member 304 having a bend or curve. In particular, the outer tubular member 304 includes a proximal linear member 306, a curved portion 308 and a distal linear member 310. Upon final assembly, the distal linear member 310 is positioned at an angle ε with respect to proximal linear member 306. An inner tubular member (not shown) can be positioned and shaped with respect to the outer tubular member 304, so as to allow rotation of the inner tubular member and thus effectuate cutting using instrument 300.

The surgical systems and methods of the present disclosure provide a marked improvement over previous brain tumor surgical techniques. The cutting implement, including the cutting window and cutting tip, can safely remove selected brain tumor tissue, but not damage the surrounding tissues. Further, with selective variable aspiration, the brain tumor tissue can be isolated from the surrounding tissue for subsequent removal and more aggressive cutting. Further, the ability to rotate the outer member assists in protecting the delicate brain anatomy tissue (e.g., dura, arachnoid, pia, etc.).

Although the present disclosure has been described with reference to preferred embodiments, workers skilled in the art will recognize that changes can be made in form and detail without departing from the spirit and scope of the present disclosure.

What is claimed is:

1. A surgical method for treating a brain tumor of a patient, the method comprising:
    providing a surgical system including a surgical instrument comprising:
        an inner member including a distal cutting tip,
        an outer member having a distal region including a distal surface forming a cutting window defined by two semicircular ends connected by two arcuate portions,
        wherein the distal region includes a tubular surface disposed about a central axis, wherein the distal surface extends from the tubular surface,
        wherein the distal surface is conically shaped, extending from the tubular surface to a tip end at an angle defined with respect to a distal axis perpendicular to the central axis,
        wherein the inner member is rotatably received within the outer member such that the cutting tip is exposed at the cutting window, the cutting tip and the distal region combining to define a cutting implement;
    creating an opening through a skull of the patient to provide external access to a target site at which the brain tumor is located;
    delivering the cutting implement through the opening and to the target site;
    plunging the surgical instrument toward the target site such that at least a portion of the tumor enters the cutting window;
    placing the cutting tip into contact with the tumor;
    moving the inner member relative to the outer member to cause the cutting tip to cut tissue of the tumor;
    selectively aspirating the target site to remove the cut tumor tissue.

2. The method of claim 1, wherein the angle is less than 45°.

3. The method of claim 1, wherein the angle is between 10° and 20°.

4. The method of claim 1, wherein the distal surface is substantially perpendicular to the central axis.

5. The method of claim 1, wherein the distal cutting tip includes an aperture that is similar in shape to the cutting window of the distal region.

6. The method of claim 5, wherein the distal cutting tip includes a distal surface that is conically shaped, extending from a tubular surface of the cutting tip to a tip end.

7. The method of claim 1, wherein the surgical instrument further includes a handpiece maintaining the inner and outer members, and an actuator adapted to cause the outer member to rotate relative to the inner member, and further wherein the cutting window is rotated by a user grasping the handpiece in a hand of the user and manipulating the actuator with a finger of the hand.

8. The method of claim 1, wherein the outer member forms a bend.

9. The method of claim 1, wherein moving the inner member to cause the cutting tip to cut tissue of the tumor includes oscillating the inner member relative to the outer member.

10. A surgical system for debriding a brain tumor, the system comprising:
    a surgical cutting instrument including:
        an inner member including a distal cutting tip,
        an outer member having a distal region forming a cutting window defined by two semicircular ends connected by two arcuate portions,
        a handpiece maintaining the inner and outer members such that the inner member is rotatably received within the outer member, with the cutting tip being exposed at the cutting window,
        wherein the distal region includes a tubular surface disposed about a central axis, wherein the distal surface extends from the tubular surface,
        wherein the distal surface is conically shaped, extending from the tubular surface to a tip end at an angle defined with respect to a distal axis perpendicular to the central axis,
        wherein the cutting tip and the distal region combine to define a cutting implement
    an aspiration control device maintained by the handpiece;
    a motor connected to the inner member for moving the inner member relative to the outer member; and
    a source of negative pressure fluidly connected to the cutting implement by a fluid pathway;
    wherein the aspiration control device is fluidly connected to the fluid pathway for providing user control over a level of vacuum applied at the cutting implement.

11. The surgical system of claim 10, wherein the angle is less than 45°.

12. The surgical system of claim 10, wherein the angle is between 10° and 20°.

13. The surgical system of claim 10, wherein the distal surface is substantially perpendicular to the central axis.

14. The surgical system of claim 10, wherein the distal cutting tip includes an aperture that is similar in shape to the cutting window of the distal region.

15. The surgical system of claim 14, wherein the distal cutting tip includes a distal surface that is conically shaped, extending from a tubular surface of the cutting tip to a tip end.

16. The surgical system of claim 10, wherein the surgical instrument further includes a handpiece maintaining the inner and outer members, and an actuator adapted to cause the outer member to rotate relative to the inner member, and further wherein the cutting window is rotated by a user grasping the handpiece in a hand of the user and manipulating the actuator with a finger of the hand.

17. The surgical system of claim 10, wherein the outer member forms a bend.

18. A surgical system for debriding a brain tumor, the system comprising:
    a surgical cutting instrument including:
        an inner member including a distal cutting tip defining a first tubular surface about a first central axis and a first distal surface extending from the first tubular surface, the first distal surface being conically shaped and extending from the first tubular surface at a first angle relative to a first distal axis perpendicular to the first central axis;

an outer member having a distal region forming a cutting window defined by two semicircular ends connected by two arcuate portions and defining a second tubular surface about a second central axis and a second distal surface extending from the second tubular surface, the second distal surface being conically shaped and extending from the second tubular surface at a second angle relative to a second distal axis perpendicular to the first central axis;

a handpiece maintaining the inner and outer members such that the inner member is rotatably received within the outer member, with the cutting tip being exposed at the cutting window, wherein the cutting tip and the distal region combine to define a cutting implement, an aspiration control device maintained by the handpiece;

a motor connected to the inner member for moving the inner member relative to the outer member; and a source of negative pressure fluidly connected to the cutting implement by a fluid pathway;

wherein the aspiration control device is fluidly connected to the fluid pathway for providing user control over a level of vacuum applied at the cutting implement.

19. The surgical system of claim 18, wherein the first angle and the second angle are less than 45°.

20. The surgical system of claim 18, wherein the first angle and the second angle are between 10° and 20°.

21. The surgical system of claim 18, wherein the distal cutting tip includes an aperture that is similar in shape to the cutting window of the distal region.

22. The surgical system of claim 18, wherein the surgical instrument further includes a handpiece maintaining the inner and outer members, and an actuator adapted to cause the outer member to rotate relative to the inner member, and further wherein the cutting window is rotated by a user grasping the handpiece in a hand of the user and manipulating the actuator with a finger of the hand.

23. The surgical system of claim 18, wherein the outer member forms a bend.

* * * * *